US009353387B2

(12) United States Patent
Jansen et al.

(10) Patent No.: US 9,353,387 B2
(45) Date of Patent: May 31, 2016

(54) DICARBOXYLIC ACID PRODUCTION PROCESS

(75) Inventors: Mickel Leonardus August Jansen, The Hague (NL); Maarten Job Van de Graaf, Zoetermeer (NL); René Verwaal, Nootdorp (NL)

(73) Assignee: DSM IP ASSETS B.V., Heerlen (NL)

( * ) Notice: Subject to any disclaimer, the term of this patent is extended or adjusted under 35 U.S.C. 154(b) by 294 days.

(21) Appl. No.: 13/260,691

(22) PCT Filed: Mar. 23, 2010

(86) PCT No.: PCT/EP2010/053753
§ 371 (c)(1), (2), (4) Date: Nov. 7, 2011

(87) PCT Pub. No.: WO2010/118932
PCT Pub. Date: Oct. 21, 2010

(65) Prior Publication Data

US 2012/0040422 A1 Feb. 16, 2012

Related U.S. Application Data

(60) Provisional application No. 61/239,566, filed on Sep. 3, 2009.

(30) Foreign Application Priority Data

Apr. 15, 2009 (EP) .................................... 09157964
Sep. 3, 2009 (EP) .................................... 09169412

(51) Int. Cl.
*C12P 7/46* (2006.01)

(52) U.S. Cl.
CPC ....................................... *C12P 7/46* (2013.01)

(58) Field of Classification Search
None
See application file for complete search history.

(56) References Cited

U.S. PATENT DOCUMENTS

| | | | | |
|---|---|---|---|---|
| 2008/0090273 | A1 | 4/2008 | Winkler et al. | |
| 2011/0081694 | A1 | 4/2011 | Verwaal et al. | |
| 2011/0104771 | A1 | 5/2011 | Verwall et al. | |
| 2011/0143405 | A1 | 6/2011 | Verwaal et al. | |
| 2011/0229945 | A1* | 9/2011 | Jansen et al. | 435/145 |
| 2012/0165569 | A1* | 6/2012 | Verwaal et al. | 562/590 |
| 2013/0171704 | A1* | 7/2013 | Jansen et al. | 435/135 |
| 2014/0031587 | A1* | 1/2014 | Verwaal et al. | 562/590 |
| 2014/0065680 | A1* | 3/2014 | Verwaal et al. | 435/145 |

FOREIGN PATENT DOCUMENTS

| | | |
|---|---|---|
| WO | 2007/061590 | 5/2007 |
| WO | 2008/128522 | 10/2008 |
| WO | 2009/065778 | 5/2009 |
| WO | 2009/065779 | 5/2009 |
| WO | 2009/101180 | 8/2009 |

OTHER PUBLICATIONS

Arikawa et al., "Effect of gene disruptions of the TCA cycle on production of succinic acid in *Saccharomyces cerevisiae*", Journal of Bioscience and Bioengineering, 87(1): 28-36 (1999).*
International Search Report for PCT/EP2010/053753 Mailed July 27, 2010.
Otero et al., "Metabolic Engineering of *Saccharomyces cerevisiae* Microbial Cell Factories for Succinic Acid Production," Journal of Biotechnology, vol. 131S, p. S205, (2007).
Camarasa et al., "Role in Anaerobiosis of the Isoenzymes for *Saccharomyces Cerevisiae* Fumarate Reductase Encoded by OSM1 and FRDS1," Yeast, vol. 24, pp. 391-401, (2007).
De Jongh, "Organic Acid Production by Aspergillus Niger / Chapter 6: Efforts Towards Engineering a Succinate Producing A. Niger Strain," BioCentrum—DTU, Technical University of Denmark, pp. 48-63, (2006).
Moon et al., "Metabolic Engeering of *Escherichia coli* for the Production of Malic Acid," Biochemical Engeering Journal, vol. 40, pp. 312-320, (2008).
Wu et al., "Enhanced Anaerobic Succinic Acid Product by *Escherichia coli* NZN111 Aerobically Grown on Gluconeogenic Carbon Sources," Enzyme and Microbial Technology, vol. 44, pp. 165-169, (2009).
Hong et al., "M. Succiniciproducens Protein," Database Geneseq Accession No. ADY72725, XP002544596, p. 1, (May 19, 2005).
Peters et al., "Trypanosoma Brucei Fumarate Reductase Protein Sequence, SED ID 10," Database Geneseq Accession No. ASQ26896, XP002544597, pp. 1-2, (Sep. 4, 2008).
Puzio et al., "Sequence 9800 From Patent WO2008142034," Database Geneseq Accession No. GM962846, XP002544598, p. 1, (Dec. 17, 2008).
De Hulster et al., "*Saccharomyces* Crevisiae Malate Dehydrogenase, SED ID 13," Database Geneseq Accession No. AWF81162, XP002544599, pp. 1-2, (Apr. 2, 2009).
Grobler et al., "Malate Permease," Database Geneseq Accession No. AAW06355, XP002544600, pp. 1-2, (Jun. 15, 2007).
Huh et al., "Effective Purification of Succinic Acid From Fermentation Broth Produced by Mannheimia Succiniciproducens," Process Biochemistry, vol. 41, pp. 1461-1465, (2006).
Song et al., "Recovery of Succinic Acid Produced by Fermentation of a Metabolically Engineered Mannheimia Succiniciproducens Strain," Journal of Biotechnology, vol. 132, pp. 445-452, (2007).
Da Silva et al., "Glucerol: A promising and abundant carbon source for industrial microbiology." Biotechnology Advances 27(2009) 30-39.
Abbot et al., "Metabolic engineering of Saccharomyces cerevisiae for production of carboxylic acids: current status and challenges." FEMS Yeast Research 9(2009) 1123-1136, XP002557537.

* cited by examiner

*Primary Examiner* — Anand Desai
(74) *Attorney, Agent, or Firm* — McBee Moore Woodward & Vanik IP, LLC

(57) ABSTRACT

The present invention relates to a process for the production of a dicarboxylic acid and ethanol which comprises fermenting a genetically modified yeast in a suitable fermentation medium under anaerobic conditions at a pH value of between 1 and 5 and producing the dicarboxylic acid and ethanol. The invention also relates to a process for crystallizing succinic acid from an aqueous solution having a pH of between 1 and 5 and comprising succinic acid, comprising removing part of the aqueous solution by evaporation to obtain a concentrated solution, and bringing the temperature of the concentrated solution to a value of between 10 and 30 degrees Celsius, wherein succinic acid crystals are formed.

12 Claims, No Drawings

SEQUENCE LISTING

```
<160> NUMBER OF SEQ ID NOS: 10

<210> SEQ ID NO 1
<211> LENGTH: 3148
<212> TYPE: DNA
<213> ORGANISM: Artificial Sequence
<220> FEATURE:
<223> OTHER INFORMATION: Synthetic construct TDH1p-PCKm-TDH1t for
      expression in S. cerevisiae

<400> SEQUENCE: 1

ggatcccttc ccttttacag tgcttcggaa aagcacagcg ttgtccaagg gaacaatttt      60

tcttcaagtt aatgcataag aaatatcttt ttttatgttt agctaagtaa aagcagcttg     120

gagtaaaaaa aaaaatgagt aaatttctcg atggattagt ttctcacagg taacataaca     180

aaaaccaaga aaagcccgct tctgaaaact acagttgact tgtatgctaa agggccagac     240

taatgggagg agaaaaagaa acgaatgtat atgctcattt acactctata tcaccatatg     300

gaggataagt tgggctgagc ttctgatcca atttattcta tccattagtt gctgatatgt     360

cccaccagcc aacacttgat agtatctact cgccattcac ttccagcagc gccagtaggg     420

ttgttgagct tagtaaaaat gtgcgcacca caagcctaca tgactccacg tcacatgaaa     480

ccacaccgtg gggccttgtt gcgctaggaa taggatatgc gacgaagacg cttctgctta     540
```

```
gtaaccacac cacattttca gggggtcgat ctgcttgctt cctttactgt cacgagcggc    600
ccataatcgc gctttttttt taaaaggcgc gagacagcaa acaggaagct cgggtttcaa    660
ccttcggagt ggtcgcagat ctggagactg gatctttaca atacagtaag gcaagccacc    720
atctgcttct taggtgcatg cgacggtatc cacgtgcaga acaacatagt ctgaagaagg    780
gggggaggag catgttcatt ctctgtagca gtaagagctt ggtgataatg accaaaactg    840
gagtctcgaa atcatataaa tagacaatat attttcacac aatgagattt gtagtacagt    900
tctattctct ctcttgcata aataagaaat tcatcaagaa cttggtttga tatttcacca    960
acacacacaa aaaacagtac ttcactaaat ttacacacaa aacaaaatga ccgatttgaa   1020
ccaattgact caagaattgg gtgctttggg tattcacgat gtccaagaag ttgtctacaa   1080
cccatcttac gaattgttgt ttgctgaaga aaccaagcca ggtttggaag gttacgaaaa   1140
gggtactgtt accaaccaag gtgctgttgc tgtcaacacc ggtatcttca ccggtcgttc   1200
tccaaaggac aaatacattg tcttggatga caagaccaag gacactgtct ggtggacttc   1260
tgaaaaggtc aagaacgaca acaaaccaat gtcccaagac acttggaact ctttaaaggg   1320
tttagtcgct gaccaattgt ctggtaagag attattcgtt gtcgatgctt tctgtggtgc   1380
caacaaggac accagattag ctgtcagagt tgtcactgaa gttgcttggc aagctcactt   1440
cgttaccaac atgttcatca gaccatctgc tgaagaattg aaaggtttca agccagattt   1500
cgttgtcatg aacggtgcca aatgtaccaa cccaaactgg aaggaacaag gtttgaactc   1560
tgaaaacttt gttgctttca acatcactga aggtgttcaa ttgattggtg gtacctggta   1620
cggtggtgaa atgaagaagg gtatgttctc catgatgaac tacttcttgc cattgagagg   1680
tattgcttcc atgcactgtt ctgccaatgt cggtaaggac ggtgacactg ccatcttctt   1740
cggtctatcc ggtaccggta agaccacttt gtccactgac ccaaagagac aattgattgg   1800
tgatgacgaa cacggttggg atgacgaagg tgttttcaac tttgaaggtg gttgttacgc   1860
caagaccatc aacttatctg ctgaaaatga accagatatc tacggtgcca tcaagcgtga   1920
cgctctattg gaaaacgttg ttgttttgga caatggtgac gtcgattatg ctgacggttc   1980
caagactgaa aacaccagag tttcttaccc aatctaccat attcaaaaca ttgtcaagcc   2040
agtttccaag gctggtccag ctaccaaagt tatcttcttg tctgctgatg ctttcggtgt   2100
tttgcctcct gtttccaagt tgactccaga acaaaccaag tactacttct tgtctggttt   2160
caccgccaag ttggctggta ctgaaagagg tatcactgaa ccaactccaa ctttctctgc   2220
ttgtttcggt gctgcctttt tgtctttgca cccaactcaa tacgctgaag ttttggtcaa   2280
gagaatgcaa gaatctggtg ctgaagctta cttggtcaac actggttgga acggtaccgg   2340
taagagaatc tccatcaaag ataccagagg tatcatcgat gccatcttgg atggttccat   2400
tgacaaggct gaaatgggtt ctttgccaat tttcgatttc tccattccaa aggctttgcc   2460
aggtgtcaac ccagccatct tagacccaag agacacctac gctgacaaag ctcaatggga   2520
agaaaaggct caagacttgg ctggtagatt cgtcaagaac ttcgaaaaat acactggtac   2580
tgctgaaggt caagctttgg ttgctgctgg tccaaaggcc taaggcccgg gcataaagca   2640
atcttgatga ggataatgat tttttttga atatacataa atactaccgt tttctgcta   2700
gattttgtga agacgtaaat aagtacatat tactttttaa gccaagacaa gattaagcat   2760
taactttacc cttttctctt ctaagtttca atactagtta tcactgttta aaagttatgg   2820
cgagaacgtc ggcggttaaa atatattacc ctgaacgtgg tgaattgaag ttctaggatg   2880
```

-continued

```
gtttaaagat ttttcctttt tgggaaataa gtaaacaata tattgctgcc tttgcaaaac   2940

gcacataccc acaatatgtg actattggca aagaacgcat tatcctttga agaggtggat   3000

actgatacta agagagtctc tattccggct ccacttttag tccagagatt acttgtcttc   3060

ttacgtatca gaacaagaaa gcatttccaa agtaattgca tttgcccttg agcagtatat   3120

atatactaag aaggcgcgcc gcggccgc                                      3148


<210> SEQ ID NO 2
<211> LENGTH: 5037
<212> TYPE: DNA
<213> ORGANISM: Artificial Sequence
<220> FEATURE:
<223> OTHER INFORMATION: Synthetic construct TDH3p-FRDm1-TDH3t for
      expression in S. cerevisiae

<400> SEQUENCE: 2

ggatccggcg cgccctattt tcgaggacct tgtcaccttg agcccaagag agccaagatt     60

taaattttcc tatgacttga tgcaaattcc caaagctaat aacatgcaag acacgtacgg    120

tcaagaagac atatttgacc tcttaacagg ttcagacgcg actgcctcat cagtaagacc    180

cgttgaaaag aacttacctg aaaaaaacga atatatacta gcgttgaatg ttagcgtcaa    240

caacaagaag tttaatgacg cggaggccaa ggcaaaaaga ttccttgatt acgtaaggga    300

gttagaatca ttttgaataa aaaacacgct tttcagttc gagtttatca ttatcaatac    360

tgccatttca aagaatacgt aaataattaa tagtagtgat ttcctaact ttatttagtc    420

aaaaaattag ccttttaatt ctgctgtaac ccgtacatgc ccaaaatagg gggcgggtta    480

cacagaatat ataacatcgt aggtgtctgg gtgaacagtt tattcctggc atccactaaa    540

tataatggag cccgcttttt aagctggcat ccagaaaaaa aaagaatccc agcaccaaaa    600

tattgttttc ttcaccaacc atcagttcat aggtccattc tcttagcgca actacagaga    660

acaggggcac aaacaggcaa aaaacgggca caacctcaat ggagtgatgc aacctgcctg    720

gagtaaatga tgacacaagg caattgaccc acgcatgtat ctatctcatt ttcttacacc    780

ttctattacc ttctgctctc tctgatttgg aaaaagctga aaaaaaaggt tgaaaccagt    840

tccctgaaat tattccccta cttgactaat aagtatataa agacggtagg tattgattgt    900

aattctgtaa atctatttct taaacttctt aaattctact tttatagtta gtcttttttt    960

tagttttaaa acaccaagaa cttagtttcg aataaacaca cataaacaaa caaaatgggt   1020

gctgatggta tttcttctgc ttccattgtt gttactgacc cagaagctgc tgccaagaag   1080

cgtgacagaa tggccagaga attgttgtcc tccaactctg gtctatgtca agaagatgaa   1140

ccaaccatca tcaacttaaa gggtttggaa cacaccattc catacagatt ggccgttgtt   1200

ttgtgtaact ccagatccac tggtgaattc gaagccaagg ctgctgaaat cttgagaaag   1260

gctttccaca tggttgacta ctctttgaat tgtttcaacc cagaatctga attgtcccgt   1320

gtcaactctt taccagtcgg tgaaaagcac caaatgtccg aagatctaag acatgtcatg   1380

gaatgtacca tttctgtcca ccactcctct ggtatgggtt tcgacccagc tgctggtcca   1440

atcatctcca gattgagagg tgccatgaga gatcacaacg acatgtccga tatctccgtc   1500

actgaagctg aagttgaatt attctctttg gctcaatctt tcgatgtcga cttggaagaa   1560

ggtactattg ccagaaagca ctctgaagcc agattggatt tgggtggtgt caacaagggt   1620

tacactgttg actacgttgt tgaccatttg agagctgctg gtatgccaaa cgtcttgttc   1680

gaatggggtg gtgatatcag agcttctggt agaaacatca agggtaactt gtggctgtt   1740
```

-continued

```
gccatcaagc gtccaccatc tgttgaagaa gttatccgtc gtgccaaggg taagatgtta   1800
aagatgggtg aagaagaaca agaagaaaag gacgatgact ctccatcttt gttgcacgtt   1860
gttgaattgg atgacgaagc tttgtgtacc tctggtgact acgaaaacgt cttataccat   1920
ccaaagcacg gtgttgctgg ttccattttc gactggcaac gtcgtggttt attgtctcca   1980
gaagaaggtg ctttagctca agtttccgtc aaatgttact ctgccatgta cgctgatgct   2040
ttggccactg tttgtttggt caagagagat gctgtcagaa tcagatactt gttggaaggt   2100
tggagatacg tcagatctcg tgtcaccaac tacttcgctt acaccagaca aggtgaaaga   2160
ttggctcaca tgcacgaaat tgctcaagaa accagagaat taagagaaat cagaattgct   2220
ggttctttgc catccagaat tgttatcgtc ggtggtggtt tggctggtct atccgctgcc   2280
attgaagctg cttcttgtgg tgctcaagtc attttgatgg aaaaggaagg tagaattggt   2340
ggtaactctg ccaaggctac ctctggtatc aacggttggg gtaccagaac ccaagccaag   2400
tctgatatct tggatggtgg taagtacttt gaaagagaca ctttcttgtc cggtgtcggt   2460
ggtaccactg acccagcttt ggtcaaggtc ttgtccgtca aatctggtga cgctatcggt   2520
tggttaactt ctttgggtgt cccattgtcc gttttgtctc aattgggtgg tcactctttc   2580
aagagaactc acagagctcc agacaagact gatggtactc cattaccaat tggtcacacc   2640
atcatgagaa ctttggaaga tcatatcaga aacaacttgt ctgaaagagt taccatcatg   2700
acccacgttt ctgttactga attgttgcac gaaactgaca ccactccaga tggtgcttct   2760
gaagttcgtg tcaccggtgt ccgttacaga gacttgtctg atgtcgatgg tcaaccttcc   2820
aaactattgg ctgacgctgt tgttttggcc actggtggtt tctccaacga cagagaagaa   2880
aactctttgt tgtgtaaata cgctcctcat ttggcttctt tcccaactac caacggtcca   2940
tgggctactg gtgacggtgt caaattggcc acctccgttg gtgccaagtt ggttgacatg   3000
gacaaggttc aattgcaccc aactggtttg attgacccaa aggacccagc taacaccact   3060
aagatcttgg gtccagaagc tttgagaggt tctggtggta ttttgttgaa caagcaaggt   3120
aagagattcg tcaacgaatt ggacttgaga tccgttgttt ccaaggccat taacactcaa   3180
ggtaacgaat acccaggttc tggtggttgt tactttgctt actgtgtctt aaacgaagat   3240
gctaccaact tattctgtgg tggtgctttg ggtttctacg gtaagaaatt aggtttgttc   3300
caaagagctg aaactgttga agaattggcc aaattgattg gttgtgacga aggtgaattg   3360
agagacactt tggaaaaata cgaaacctgt tccaaggcca aggttgcttg tccagtcact   3420
ggtaaggttg ttttcccatg tgttgtcggt accagaggtc catacaatgt tgctttcgtc   3480
actccatcca tccactacac catgggtggt tgtttgatct ctccagctgc tgaagtcttg   3540
caagaataca agggtttgaa tatcttggaa aaccacagac caatcagatg tttgttcggt   3600
gctggtgaag tcactggtgg tgtccacggt ggtaacagat taggtggtaa ctctctattg   3660
gaatgtgttg tctttggtaa gattgctggt gacagagctg ccactatctt gcaaaagaga   3720
gaaattgctt tgtccaagac ctcctggacc tctgttgttg tcagagaatc cagatctggt   3780
gaacaattcg gtaccggttc cagagttttg agattcaact tgccaggtgc tttacaaaga   3840
accggtttga acttgggtga attcgttgcc atcagaggtg aatgggatgg tcaacaatta   3900
gtcggttact tctctccaat cactttgcca gaagatttgg gtaccatctc tttgttggtc   3960
agagctgaca agggtacttt gaaggaatgg atctgtgctt tgcgtccagg tgactccgtt   4020
gaaatcaagg cttgtggtgg tctaagaatt gaccaagatc cagtcaagaa atgtttgttg   4080
ttcagaaaca gaccaattac cagatttgct ttggttgctg ctggtaccgg tgttgctcca   4140
```

```
atgttgcaag ttatcagagc tgctttgaag aagccatacg tcgacacttt ggaatccatc   4200
agattgatct acgctgctga agaatatgac actttaacct acagatctat cttgcaaaga   4260
tttgctgaag aattcccaga caaattcgtt tgtaacttcg tcttaaacaa ccctccagaa   4320
ggttggaccg gtggtgttgg tttcgtcaac aagaaatctt tgcaaaaggt tttgcaacca   4380
ccttcttctg aaccattgat tgttgtttgt ggtccacctg ttatgcaaag agatgtcaaa   4440
aatgaattgt tgtccatggg ttacgacaag gaattggttc acactgtcga tggtgaatct   4500
ggtaccttgt aaggcccggg cgtgaattta ctttaaatct tgcatttaaa taaattttct   4560
ttttatagct ttatgactta gtttcaattt atatactatt ttaatgacat tttcgattca   4620
ttgattgaaa gctttgtgtt ttttcttgat gcgctattgc attgttcttg tctttttcgc   4680
cacatgtaat atctgtagta gatacctgat acattgtgga tgctgagtga aattttagtt   4740
aataatggag gcgctcttaa taattttggg gatattggct ttttttttta aagtttacaa   4800
atgaattttt tccgccagga taacgattct gaagttactc ttagcgttcc tatcggtaca   4860
gccatcaaat catgcctata aatcatgcct atatttgcgt gcagtcagta tcatctacat   4920
gaaaaaaact cccgcaattt cttatagaat acgttgaaaa ttaaatgtac gcgccaagat   4980
aagataacat atatctagat gcagtaatat acacagattc cggccggccg cggccgc      5037
```

<210> SEQ ID NO 3
<211> LENGTH: 2950
<212> TYPE: DNA
<213> ORGANISM: Artificial Sequence
<220> FEATURE:
<223> OTHER INFORMATION: Synthetic construct TDH1p-FUMR-TDH1t for expression in S. cerevisiae

<400> SEQUENCE: 3

```
ggatcccttc cctttacag tgcttcggaa aagcacagcg ttgtccaagg gaacaatttt     60
tcttcaagtt aatgcataag aaatatcttt ttttatgttt agctaagtaa aagcagcttg    120
gagtaaaaaa aaaaatgagt aaatttctcg atggattagt ttctcacagg taacataaca    180
aaaaccaaga aaagcccgct tctgaaaact acagttgact tgtatgctaa agggccagac    240
taatgggagg agaaaaagaa acgaatgtat atgctcattt acactctata tcaccatatg    300
gaggataagt tgggctgagc ttctgatcca atttattcta tccattagtt gctgatatgt    360
cccaccagcc aacacttgat agtatctact cgccattcac ttccagcagc gccagtaggg    420
ttgttgagct tagtaaaaat gtgcgcacca caagcctaca tgactccacg tcacatgaaa    480
ccacaccgtg gggccttgtt gcgctaggaa taggatatgc gacgaagacg cttctgctta    540
gtaaccacac cacattttca gggggtcgat ctgcttgctt cctttactgt cacgagcggc    600
ccataatcgc gctttttttt taaaaggcgc gagacagcaa acaggaagct cgggtttcaa    660
ccttcggagt ggtcgcagat ctggagactg gatctttaca atacagtaag gcaagccacc    720
atctgcttct taggtgcatg cgacggtatc cacgtgcaga acaacatagt ctgaagaagg    780
gggggaggag catgttcatt ctctgtagca gtaagagctt ggtgataatg accaaaactg    840
gagtctcgaa atcatataaa tagacaatat attttcacac aatgagattt gtagtacagt    900
tctattctct ctcttgcata aataagaaat tcatcaagaa cttggtttga tatttcacca    960
acacacacaa aaaacagtac ttcactaaat ttacacacaa aacaaaatgt cctctgcttc   1020
tgctgctttg caaaaattca gagctgaaag agataccttc ggtgacttgc aagttccagc   1080
tgaccgttac tggggtgctc aaactcaaag atctttgcaa aactttgaca ttggtggtcc   1140
```

```
aactgaaaga atgccagaac cattaatcag agctttcggt gttttgaaga aggctgctgc   1200

caccgtcaac atgacctacg gtttggaccc aaaggttggt gaagccatcc aaaaggctgc   1260

tgacgaagtt atcgatggtt ctttgattga ccatttccca ttggttgtct ggcaaaccgg   1320

ttctggtact caaaccaaga tgaacgtcaa tgaagtcatc tccaacagag ccattgaatt   1380

gttgggtggt gaattaggtt ccaaggctcc agtccaccca aacgatcatg tcaacatgtc   1440

tcaatcttcc aacgacactt tcccaactgc catgcacgtt gctgccgttg ttgaaattca   1500

cggtagattg attccagctt tgaccacttt gagagatgct ttgcaagcca aatctgctga   1560

attcgaacac atcatcaaga ttggtagaac ccacttgcaa gatgctaccc cattgacttt   1620

aggtcaagaa ttctccggtt acactcaaca attgacctac ggtattgctc gtgttcaagg   1680

tactttggaa agattataca acttggctca aggtggtact gctgtcggta ctggtttgaa   1740

caccagaaag ggtttcgatg ccaaggttgc tgaagccatt gcttccatca ctggtttacc   1800

attcaagacc gctccaaaca aattcgaagc tttggctgct cacgacgctt tggttgaagc   1860

tcacggtgct ttgaacaccg ttgcttgttc tttgatgaag attgccaacg atatccgtta   1920

cttgggttct ggtccaagat gtggtttagg tgaattgtct ctaccagaaa acgaaccagg   1980

ttcttccatc atgccaggta aggtcaaccc aactcaatgt gaagctatga ccatggtttg   2040

tgctcaagtc atgggtaaca acactgccat ctctgttgct ggttccaacg gtcaattcga   2100

attgaatgtc tttaaaccag tcatgatcaa gaacttgatc caatccatca gattaatctc   2160

tgacgcttcc atctctttca ccaagaactg tgttgtcggt attgaagcta acgaaaagaa   2220

gatctcctcc atcatgaacg aatctttgat gttggtcact gctttgaacc ctcacattgg   2280

ttacgacaag gctgccaagt gtgccaagaa ggctcacaag gaaggtacca ctttgaaaga   2340

agctgctcta tctttgggtt acttgacctc tgaagaattc gaccaatggg ttagacctga   2400

ggacatgatt tctgccaagg attaaggccc gggcataaag caatcttgat gaggataatg   2460

attttttttt gaatatacat aaatactacc gtttttctgc tagattttgt gaagacgtaa   2520

ataagtacat attacttttt aagccaagac aagattaagc attaacttta ccccttttctc   2580

ttctaagttt caatactagt tatcactgtt taaaagttat ggcgagaacg tcggcggtta   2640

aaatatatta ccctgaacgt ggtgaattga agttctagga tggtttaaag atttttcctt   2700

tttgggaaat aagtaaacaa tatattgctg cctttgcaaa acgcacatac ccacaatatg   2760

tgactattgg caaagaacgc attatccttt gaagaggtgg atactgatac taagagagtc   2820

tctattccgg ctccactttt agtccagaga ttacttgtct tcttacgtat cagaacaaga   2880

aagcatttcc aaagtaattg catttgccct tgagcagtat atatatacta agaaggcgcg   2940

ccgcggccgc                                                          2950
```

```
<210> SEQ ID NO 4
<211> LENGTH: 2637
<212> TYPE: DNA
<213> ORGANISM: Artificial Sequence
<220> FEATURE:
<223> OTHER INFORMATION: Synthetic construct TDH3p-delta12N MDH2-TDH3t
      for expression in S. cerevisiae

<400> SEQUENCE: 4

ggatccggcg cgccctattt tcgaggacct tgtcaccttg agcccaagag agccaagatt     60

taaattttcc tatgacttga tgcaaattcc caaagctaat aacatgcaag acacgtacgg    120

tcaagaagac atatttgacc tcttaacagg ttcagacgcg actgcctcat cagtaagacc    180
```

-continued

```
cgttgaaaag aacttacctg aaaaaaacga atatatacta gcgttgaatg ttagcgtcaa    240
caacaagaag tttaatgacg cggaggccaa ggcaaaaaga ttccttgatt acgtaaggga    300
gttagaatca ttttgaataa aaaacacgct ttttcagttc gagtttatca ttatcaatac    360
tgccatttca aagaatacgt aaataattaa tagtagtgat tttcctaact ttatttagtc    420
aaaaaattag ccttttaatt ctgctgtaac ccgtacatgc ccaaaatagg gggcgggtta    480
cacagaatat ataacatcgt aggtgtctgg gtgaacagtt tattcctggc atccactaaa    540
tataatggag cccgcttttt aagctggcat ccagaaaaaa aaagaatccc agcaccaaaa    600
tattgttttc ttcaccaacc atcagttcat aggtccattc tcttagcgca actacagaga    660
acaggggcac aaacaggcaa aaaacgggca caacctcaat ggagtgatgc aacctgcctg    720
gagtaaatga tgacacaagg caattgaccc acgcatgtat ctatctcatt ttcttacacc    780
ttctattacc ttctgctctc tctgatttgg aaaaagctga aaaaaaaggt tgaaaccagt    840
tccctgaaat tattccccta cttgactaat aagtatataa agacggtagg tattgattgt    900
aattctgtaa atctatttct taaacttctt aaattctact tttatagtta gtcttttttt    960
tagttttaaa acaccaagaa cttagtttcg aataaacaca cataaacaaa caaaatgttg   1020
aagattgcca tcttgggtgc tgctggtggt atcggtcaat ctttgtcttt gttgttgaag   1080
gctcaattgc aataccaatt gaaggaatcc aacagatctg ttacccacat tcatttggct   1140
ttgtacgatg tcaaccaaga agctatcaac ggtgtcactg ctgacttgtc tcacatcgat   1200
accccaatct ctgtttcctc tcactctcca gctggtggta ttgaaaactg tttgcacaac   1260
gcttccattg ttgtcattcc agccggtgtt ccaagaaagc caggtatgac ccgtgacgat   1320
ttgttcaacg tcaatgccgg tatcatctct caattaggtg attccattgc tgaatgttgt   1380
gacttgtcca aggttttcgt cttggttatc tccaacccag tcaactcttt ggttcctgtt   1440
atggtttcca acatcttgaa gaaccaccca caatccagaa actctggtat tgaaagaaga   1500
atcatgggtg tcaccaaatt ggacattgtc agagcttcca ctttcttgag agaaatcaac   1560
attgaatctg gtttgactcc aagagtcaac tccatgccag atgttccagt tatcggtggt   1620
cactctggtg aaactatcat cccattattc tctcaatcta acttcttgtc cagattgaat   1680
gaagatcaat tgaaatactt gattcaccgt gtccaatacg gtggtgacga agttgtcaag   1740
gccaagaacg gtaagggttc tgctactcta tccatggctc atgccggtta caagtgtgtt   1800
gtccaattcg tttctctatt attaggtaac attgaacaaa tccacggtac ctactacgtt   1860
ccattgaaag atgctaacaa cttcccaatt gctccaggtg ctgaccaatt attgccatta   1920
gtcgacggtg ctgactactt tgccatccca ttgaccatca ctaccaaggg tgtttcttac   1980
gttgactacg atatcgtcaa cagaatgaac gacatggaaa gaaaccaaat gttgcctatc   2040
tgtgtttctc aattgaagaa gaacattgac aagggtttgg aattcgttgc ttccagatct   2100
gcttccagtt aaggcccggg cgtgaattta ctttaaatct tgcatttaaa taaattttct   2160
ttttatagct ttatgactta gtttcaattt atatactatt ttaatgacat tttcgattca   2220
ttgattgaaa gctttgtgtt ttttcttgat gcgctattgc attgttcttg tctttttcgc   2280
cacatgtaat atctgtagta gatacctgat acattgtgga tgctgagtga aattttagtt   2340
aataatggag gcgctcttaa taattttggg gatattggct ttttttttta aagtttacaa   2400
atgaattttt tccgccagga taacgattct gaagttactc ttagcgttcc tatcggtaca   2460
gccatcaaat catgcctata aatcatgcct atatttgcgt gcagtcagta tcatctacat   2520
```

```
gaaaaaaact cccgcaattt cttatagaat acgttgaaaa ttaaatgtac gcgccaagat   2580

aagataacat atatctagat gcagtaatat acacagattc cggccggccg cggccgc      2637


<210> SEQ ID NO 5
<211> LENGTH: 2240
<212> TYPE: DNA
<213> ORGANISM: Artificial Sequence
<220> FEATURE:
<223> OTHER INFORMATION: Synthetic construct Eno1p-SpMAE1-ENOt for
      expression in S. cerevisiae

<400> SEQUENCE: 5

ggatccggcg cgccccgcgg aaccgccaga tattcattac ttgacgcaaa agcgtttgaa     60

ataatgacga aaaagaagga agaaaaaaaa agaaaaatac cgcttctagg cgggttatct    120

actgatccga gcttccacta ggatagcacc caaacacctg catatttgga cgacctttac    180

ttacaccacc aaaaaccact ttcgcctctc ccgcccctga taacgtccac taattgagcg    240

attacctgag cggtcctctt ttgtttgcag catgagactt gcatactgca aatcgtaagt    300

agcaacgtct caaggtcaaa actgtatgga aaccttgtca cctcacttaa ttctagctag    360

cctaccctgc aagtcaagag gtctccgtga ttcctagcca cctcaaggta tgcctctccc    420

cggaaactgt ggccttttct ggcacacatg atctccacga tttcaacata taaatagctt    480

ttgataatgg caatattaat caaatttatt ttacttcttt cttgtaacat ctctcttgta    540

atcccttatt ccttctagct atttttcata aaaaaccaag caactgctta tcaacacaca    600

aacactaaaa caaaatgggt gaattgaagg aaatcttgaa gcaacgttac catgaattgt    660

tggactggaa cgtcaaggct ccacacgttc cattgtctca aagattgaag catttcacct    720

ggtcctggtt tgcttgtacc atggccactg gtggtgtcgg tttgatcatt ggttctttcc    780

cattcagatt ctacggtttg aacaccattg gtaagattgt ctacatctta caaatcttct    840

tattctcttt gtttggttct tgtatgttgt tcagattcat caaataccca tctaccatca    900

aggactcctg gaaccaccac ttggaaaaat tattcattgc tacctgtttg ctatccatct    960

ccactttcat tgacatgttg gccatctacg cttacccaga cactggtgaa tggatggtct   1020

gggttatcag aatcttatac tacatctacg ttgctgtctc tttcatctac tgtgtcatgg   1080

ctttcttcac catttcaac aaccacgttt acaccattga aactgcttct ccagcttgga   1140

tcttaccaat tttcccacca atgatctgtg gtgtcattgc tggtgctgtc aactccactc   1200

aaccagctca ccaattgaag aacatggtta tcttcggtat cttattccaa ggtttgggtt   1260

tctgggttta cttgttgttg tttgctgtca acgttttgag attcttcacc gttggtttgg   1320

ccaagcctca agacagacca ggtatgttca tgtttgttgg tccaccagct ttctccggtt   1380

tggctttgat caacattgcc cgtggtgcta tgggttccag accatacatt ttcgtcggtg   1440

ccaattcttc tgaatacttg ggtttcgttt ccactttcat ggccattttc atctggggtt   1500

tggctgcttg gtgttactgt ttggccatgg tttctttctt ggctggtttc ttcaccagag   1560

ctccattgaa atttgcttgt ggttggtttg ctttcatctt cccaaacgtc ggtttcgtta   1620

actgtaccat tgaaattggt aagatgattg actccaaggc cttccaaatg ttcggtcaca   1680

tcatcggtgt catcctatgt atccaatgga tcttgttgat gtacttgatg gtcagagctt   1740

tcttggtcaa cgatttgtgt tacccaggta aggatgaaga tgctcaccca cctccaaagc   1800

caaacactgg tgttttgaac ccaactttcc caccagaaaa ggctccagct tctttggaaa   1860

aggttgacac ccacgttact tccactggtg gtgaatctga tcctccatct tctgaacacg   1920
```

```
aaagcgttta agagcttttg attaagcctt ctagtccaaa aaacacgttt ttttgtcatt   1980

tatttcattt tcttagaata gtttagttta ttcattttat agtcacgaat gttttatgat   2040

tctatatagg gttgcaaaca agcatttttc attttatgtt aaaacaattt caggtttacc   2100

ttttattctg cttgtggtga cgcgggtatc cgcccgctct tttggtcacc catgtattta   2160

attgcataaa taattcttaa aagtggagct agtctatttc tatttacata cctctcattt   2220

ctcatttcct ccgcggccgc                                               2240


<210> SEQ ID NO 6
<211> LENGTH: 538
<212> TYPE: PRT
<213> ORGANISM: Mannheimia succiniciproducens

<400> SEQUENCE: 6

Met Thr Asp Leu Asn Gln Leu Thr Gln Glu Leu Gly Ala Leu Gly Ile
1               5                   10                  15

His Asp Val Gln Glu Val Val Tyr Asn Pro Ser Tyr Glu Leu Leu Phe
            20                  25                  30

Ala Glu Glu Thr Lys Pro Gly Leu Glu Gly Tyr Glu Lys Gly Thr Val
        35                  40                  45

Thr Asn Gln Gly Ala Val Ala Val Asn Thr Gly Ile Phe Thr Gly Arg
    50                  55                  60

Ser Pro Lys Asp Lys Tyr Ile Val Leu Asp Asp Lys Thr Lys Asp Thr
65                  70                  75                  80

Val Trp Trp Thr Ser Glu Lys Val Lys Asn Asp Asn Lys Pro Met Ser
                85                  90                  95

Gln Asp Thr Trp Asn Ser Leu Lys Gly Leu Val Ala Asp Gln Leu Ser
            100                 105                 110

Gly Lys Arg Leu Phe Val Val Asp Ala Phe Cys Gly Ala Asn Lys Asp
        115                 120                 125

Thr Arg Leu Ala Val Arg Val Val Thr Glu Val Ala Trp Gln Ala His
    130                 135                 140

Phe Val Thr Asn Met Phe Ile Arg Pro Ser Ala Glu Glu Leu Lys Gly
145                 150                 155                 160

Phe Lys Pro Asp Phe Val Val Met Asn Gly Ala Lys Cys Thr Asn Pro
                165                 170                 175

Asn Trp Lys Glu Gln Gly Leu Asn Ser Glu Asn Phe Val Ala Phe Asn
            180                 185                 190

Ile Thr Glu Gly Val Gln Leu Ile Gly Gly Thr Trp Tyr Gly Gly Glu
        195                 200                 205

Met Lys Lys Gly Met Phe Ser Met Met Asn Tyr Phe Leu Pro Leu Arg
    210                 215                 220

Gly Ile Ala Ser Met His Cys Ser Ala Asn Val Gly Lys Asp Gly Asp
225                 230                 235                 240

Thr Ala Ile Phe Phe Gly Leu Ser Gly Thr Gly Lys Thr Thr Leu Ser
                245                 250                 255

Thr Asp Pro Lys Arg Gln Leu Ile Gly Asp Asp Glu His Gly Trp Asp
            260                 265                 270

Asp Glu Gly Val Phe Asn Phe Glu Gly Gly Cys Tyr Ala Lys Thr Ile
        275                 280                 285

Asn Leu Ser Ala Glu Asn Glu Pro Asp Ile Tyr Gly Ala Ile Lys Arg
    290                 295                 300

Asp Ala Leu Leu Glu Asn Val Val Val Leu Asp Asn Gly Asp Val Asp
305                 310                 315                 320
```

```
Tyr Ala Asp Gly Ser Lys Thr Glu Asn Thr Arg Val Ser Tyr Pro Ile
                325                 330                 335

Tyr His Ile Gln Asn Ile Val Lys Pro Val Ser Lys Ala Gly Pro Ala
            340                 345                 350

Thr Lys Val Ile Phe Leu Ser Ala Asp Ala Phe Gly Val Leu Pro Pro
        355                 360                 365

Val Ser Lys Leu Thr Pro Glu Gln Thr Lys Tyr Tyr Phe Leu Ser Gly
    370                 375                 380

Phe Thr Ala Lys Leu Ala Gly Thr Glu Arg Gly Ile Thr Glu Pro Thr
385                 390                 395                 400

Pro Thr Phe Ser Ala Cys Phe Gly Ala Ala Phe Leu Ser Leu His Pro
                405                 410                 415

Thr Gln Tyr Ala Glu Val Leu Val Lys Arg Met Gln Glu Ser Gly Ala
            420                 425                 430

Glu Ala Tyr Leu Val Asn Thr Gly Trp Asn Gly Thr Gly Lys Arg Ile
        435                 440                 445

Ser Ile Lys Asp Thr Arg Gly Ile Ile Asp Ala Ile Leu Asp Gly Ser
    450                 455                 460

Ile Asp Lys Ala Glu Met Gly Ser Leu Pro Ile Phe Asp Phe Ser Ile
465                 470                 475                 480

Pro Lys Ala Leu Pro Gly Val Asn Pro Ala Ile Leu Asp Pro Arg Asp
                485                 490                 495

Thr Tyr Ala Asp Lys Ala Gln Trp Glu Glu Lys Ala Gln Asp Leu Ala
            500                 505                 510

Gly Arg Phe Val Lys Asn Phe Glu Lys Tyr Thr Gly Thr Ala Glu Gly
        515                 520                 525

Gln Ala Leu Val Ala Ala Gly Pro Lys Ala
    530                 535


<210> SEQ ID NO 7
<211> LENGTH: 1164
<212> TYPE: PRT
<213> ORGANISM: Artificial Sequence
<220> FEATURE:
<223> OTHER INFORMATION: Mitochondrial Trypanosoma brucei fumarate
      reductase (FRDm1) amino acid sequence, lacking the 68 N-terminal
      residues

<400> SEQUENCE: 7

Met Ala Asp Gly Ile Ser Ser Ala Ser Ile Val Val Thr Asp Pro Glu
1               5                   10                  15

Ala Ala Ala Lys Lys Arg Asp Arg Met Ala Arg Glu Leu Leu Ser Ser
            20                  25                  30

Asn Ser Gly Leu Cys Gln Glu Asp Glu Pro Thr Ile Ile Asn Leu Lys
        35                  40                  45

Gly Leu Glu His Thr Ile Pro Tyr Arg Leu Ala Val Val Leu Cys Asn
    50                  55                  60

Ser Arg Ser Thr Gly Glu Phe Glu Ala Lys Ala Ala Glu Ile Leu Arg
65                  70                  75                  80

Lys Ala Phe His Met Val Asp Tyr Ser Leu Asn Cys Phe Asn Pro Glu
                85                  90                  95

Ser Glu Leu Ser Arg Val Asn Ser Leu Pro Val Gly Glu Lys His Gln
            100                 105                 110

Met Ser Glu Asp Leu Arg His Val Met Glu Cys Thr Ile Ser Val His
        115                 120                 125
```

```
His Ser Ser Gly Met Gly Phe Asp Pro Ala Ala Gly Pro Ile Ile Ser
    130                 135                 140

Arg Leu Arg Gly Ala Met Arg Asp His Asn Asp Met Ser Asp Ile Ser
145                 150                 155                 160

Val Thr Glu Ala Glu Val Glu Leu Phe Ser Leu Ala Gln Ser Phe Asp
                165                 170                 175

Val Asp Leu Glu Glu Gly Thr Ile Ala Arg Lys His Ser Glu Ala Arg
            180                 185                 190

Leu Asp Leu Gly Gly Val Asn Lys Gly Tyr Thr Val Asp Tyr Val Val
        195                 200                 205

Asp His Leu Arg Ala Ala Gly Met Pro Asn Val Leu Phe Glu Trp Gly
    210                 215                 220

Gly Asp Ile Arg Ala Ser Gly Arg Asn Ile Lys Gly Asn Leu Trp Ala
225                 230                 235                 240

Val Ala Ile Lys Arg Pro Pro Ser Val Glu Glu Val Ile Arg Arg Ala
                245                 250                 255

Lys Gly Lys Met Leu Lys Met Gly Glu Glu Glu Gln Glu Glu Lys Asp
            260                 265                 270

Asp Asp Ser Pro Ser Leu Leu His Val Val Glu Leu Asp Asp Glu Ala
        275                 280                 285

Leu Cys Thr Ser Gly Asp Tyr Glu Asn Val Leu Tyr His Pro Lys His
    290                 295                 300

Gly Val Ala Gly Ser Ile Phe Asp Trp Gln Arg Arg Gly Leu Leu Ser
305                 310                 315                 320

Pro Glu Glu Gly Ala Leu Ala Gln Val Ser Val Lys Cys Tyr Ser Ala
                325                 330                 335

Met Tyr Ala Asp Ala Leu Ala Thr Val Cys Leu Val Lys Arg Asp Ala
            340                 345                 350

Val Arg Ile Arg Tyr Leu Leu Glu Gly Trp Arg Tyr Val Arg Ser Arg
        355                 360                 365

Val Thr Asn Tyr Phe Ala Tyr Thr Arg Gln Gly Glu Arg Leu Ala His
    370                 375                 380

Met His Glu Ile Ala Gln Glu Thr Arg Glu Leu Arg Glu Ile Arg Ile
385                 390                 395                 400

Ala Gly Ser Leu Pro Ser Arg Ile Val Ile Val Gly Gly Gly Leu Ala
                405                 410                 415

Gly Leu Ser Ala Ala Ile Glu Ala Ala Ser Cys Gly Ala Gln Val Ile
            420                 425                 430

Leu Met Glu Lys Glu Gly Arg Ile Gly Gly Asn Ser Ala Lys Ala Thr
        435                 440                 445

Ser Gly Ile Asn Gly Trp Gly Thr Arg Thr Gln Ala Lys Ser Asp Ile
    450                 455                 460

Leu Asp Gly Gly Lys Tyr Phe Glu Arg Asp Thr Phe Leu Ser Gly Val
465                 470                 475                 480

Gly Gly Thr Thr Asp Pro Ala Leu Val Lys Val Leu Ser Val Lys Ser
                485                 490                 495

Gly Asp Ala Ile Gly Trp Leu Thr Ser Leu Gly Val Pro Leu Ser Val
            500                 505                 510

Leu Ser Gln Leu Gly Gly His Ser Phe Lys Arg Thr His Arg Ala Pro
        515                 520                 525

Asp Lys Thr Asp Gly Thr Pro Leu Pro Ile Gly His Thr Ile Met Arg
    530                 535                 540

Thr Leu Glu Asp His Ile Arg Asn Asn Leu Ser Glu Arg Val Thr Ile
```

```
545                 550                 555                 560

Met Thr His Val Ser Val Thr Glu Leu Leu His Glu Thr Asp Thr Thr
                565                 570                 575

Pro Asp Gly Ala Ser Glu Val Arg Val Thr Gly Val Arg Tyr Arg Asp
            580                 585                 590

Leu Ser Asp Val Asp Gly Gln Pro Ser Lys Leu Leu Ala Asp Ala Val
        595                 600                 605

Val Leu Ala Thr Gly Gly Phe Ser Asn Asp Arg Glu Glu Asn Ser Leu
    610                 615                 620

Leu Cys Lys Tyr Ala Pro His Leu Ala Ser Phe Pro Thr Thr Asn Gly
625                 630                 635                 640

Pro Trp Ala Thr Gly Asp Gly Val Lys Leu Ala Thr Ser Val Gly Ala
                645                 650                 655

Lys Leu Val Asp Met Asp Lys Val Gln Leu His Pro Thr Gly Leu Ile
            660                 665                 670

Asp Pro Lys Asp Pro Ala Asn Thr Thr Lys Ile Leu Gly Pro Glu Ala
        675                 680                 685

Leu Arg Gly Ser Gly Gly Ile Leu Leu Asn Lys Gln Gly Lys Arg Phe
    690                 695                 700

Val Asn Glu Leu Asp Leu Arg Ser Val Val Ser Lys Ala Ile Asn Thr
705                 710                 715                 720

Gln Gly Asn Glu Tyr Pro Gly Ser Gly Gly Cys Tyr Phe Ala Tyr Cys
                725                 730                 735

Val Leu Asn Glu Asp Ala Thr Asn Leu Phe Cys Gly Gly Ala Leu Gly
            740                 745                 750

Phe Tyr Gly Lys Lys Leu Gly Leu Phe Gln Arg Ala Glu Thr Val Glu
        755                 760                 765

Glu Leu Ala Lys Leu Ile Gly Cys Asp Glu Gly Glu Leu Arg Asp Thr
    770                 775                 780

Leu Glu Lys Tyr Glu Thr Cys Ser Lys Ala Lys Val Ala Cys Pro Val
785                 790                 795                 800

Thr Gly Lys Val Val Phe Pro Cys Val Val Gly Thr Arg Gly Pro Tyr
                805                 810                 815

Asn Val Ala Phe Val Thr Pro Ser Ile His Tyr Thr Met Gly Gly Cys
            820                 825                 830

Leu Ile Ser Pro Ala Ala Glu Val Leu Gln Glu Tyr Lys Gly Leu Asn
        835                 840                 845

Ile Leu Glu Asn His Arg Pro Ile Arg Cys Leu Phe Gly Ala Gly Glu
    850                 855                 860

Val Thr Gly Gly Val His Gly Gly Asn Arg Leu Gly Gly Asn Ser Leu
865                 870                 875                 880

Leu Glu Cys Val Val Phe Gly Lys Ile Ala Gly Asp Arg Ala Ala Thr
                885                 890                 895

Ile Leu Gln Lys Arg Glu Ile Ala Leu Ser Lys Thr Ser Trp Thr Ser
            900                 905                 910

Val Val Val Arg Glu Ser Arg Ser Gly Glu Gln Phe Gly Thr Gly Ser
        915                 920                 925

Arg Val Leu Arg Phe Asn Leu Pro Gly Ala Leu Gln Arg Thr Gly Leu
    930                 935                 940

Asn Leu Gly Glu Phe Val Ala Ile Arg Gly Glu Trp Asp Gly Gln Gln
945                 950                 955                 960

Leu Val Gly Tyr Phe Ser Pro Ile Thr Leu Pro Glu Asp Leu Gly Thr
                965                 970                 975
```

```
Ile Ser Leu Leu Val Arg Ala Asp Lys Gly Thr Leu Lys Glu Trp Ile
            980                 985                 990

Cys Ala Leu Arg Pro Gly Asp Ser  Val Glu Ile Lys Ala  Cys Gly Gly
        995                 1000                 1005

Leu Arg  Ile Asp Gln Asp Pro  Val Lys Lys Cys Leu  Leu Phe Arg
    1010                 1015                 1020

Asn Arg  Pro Ile Thr Arg Phe  Ala Leu Val Ala Ala  Gly Thr Gly
    1025                 1030                 1035

Val Ala  Pro Met Leu Gln Val  Ile Arg Ala Ala Leu  Lys Lys Pro
    1040                 1045                 1050

Tyr Val  Asp Thr Leu Glu Ser  Ile Arg Leu Ile Tyr  Ala Ala Glu
    1055                 1060                 1065

Glu Tyr  Asp Thr Leu Thr Tyr  Arg Ser Ile Leu Gln  Arg Phe Ala
    1070                 1075                 1080

Glu Glu  Phe Pro Asp Lys Phe  Val Cys Asn Phe Val  Leu Asn Asn
    1085                 1090                 1095

Pro Pro  Glu Gly Trp Thr Gly  Gly Val Gly Phe Val  Asn Lys Lys
    1100                 1105                 1110

Ser Leu  Gln Lys Val Leu Gln  Pro Pro Ser Ser Glu  Pro Leu Ile
    1115                 1120                 1125

Val Val  Cys Gly Pro Pro Val  Met Gln Arg Asp Val  Lys Asn Glu
    1130                 1135                 1140

Leu Leu  Ser Met Gly Tyr Asp  Lys Glu Leu Val His  Thr Val Asp
    1145                 1150                 1155

Gly Glu  Ser Gly Thr Leu
    1160

<210> SEQ ID NO 8
<211> LENGTH: 472
<212> TYPE: PRT
<213> ORGANISM: Artificial Sequence
<220> FEATURE:
<223> OTHER INFORMATION: Rhizopus oryzae fumarase amino acid sequence,
      lacking first 23 amino acids,

<400> SEQUENCE: 8

Met Ser Ser Ala Ser Ala Ala Leu Gln Lys Phe Arg Ala Glu Arg Asp
1               5                   10                  15

Thr Phe Gly Asp Leu Gln Val Pro Ala Asp Arg Tyr Trp Gly Ala Gln
            20                  25                  30

Thr Gln Arg Ser Leu Gln Asn Phe Asp Ile Gly Gly Pro Thr Glu Arg
        35                  40                  45

Met Pro Glu Pro Leu Ile Arg Ala Phe Gly Val Leu Lys Lys Ala Ala
    50                  55                  60

Ala Thr Val Asn Met Thr Tyr Gly Leu Asp Pro Lys Val Gly Glu Ala
65                  70                  75                  80

Ile Gln Lys Ala Ala Asp Glu Val Ile Asp Gly Ser Leu Ile Asp His
                85                  90                  95

Phe Pro Leu Val Val Trp Gln Thr Gly Ser Gly Thr Gln Thr Lys Met
            100                 105                 110

Asn Val Asn Glu Val Ile Ser Asn Arg Ala Ile Glu Leu Leu Gly Gly
        115                 120                 125

Glu Leu Gly Ser Lys Ala Pro Val His Pro Asn Asp His Val Asn Met
    130                 135                 140

Ser Gln Ser Ser Asn Asp Thr Phe Pro Thr Ala Met His Val Ala Ala
```

```
145                 150                 155                 160

Val Val Glu Ile His Gly Arg Leu Ile Pro Ala Leu Thr Thr Leu Arg
                165                 170                 175

Asp Ala Leu Gln Ala Lys Ser Ala Glu Phe Glu His Ile Ile Lys Ile
            180                 185                 190

Gly Arg Thr His Leu Gln Asp Ala Thr Pro Leu Thr Leu Gly Gln Glu
        195                 200                 205

Phe Ser Gly Tyr Thr Gln Gln Leu Thr Tyr Gly Ile Ala Arg Val Gln
    210                 215                 220

Gly Thr Leu Glu Arg Leu Tyr Asn Leu Ala Gln Gly Gly Thr Ala Val
225                 230                 235                 240

Gly Thr Gly Leu Asn Thr Arg Lys Gly Phe Asp Ala Lys Val Ala Glu
                245                 250                 255

Ala Ile Ala Ser Ile Thr Gly Leu Pro Phe Lys Thr Ala Pro Asn Lys
            260                 265                 270

Phe Glu Ala Leu Ala Ala His Asp Ala Leu Val Glu Ala His Gly Ala
        275                 280                 285

Leu Asn Thr Val Ala Cys Ser Leu Met Lys Ile Ala Asn Asp Ile Arg
    290                 295                 300

Tyr Leu Gly Ser Gly Pro Arg Cys Gly Leu Gly Glu Leu Ser Leu Pro
305                 310                 315                 320

Glu Asn Glu Pro Gly Ser Ser Ile Met Pro Gly Lys Val Asn Pro Thr
                325                 330                 335

Gln Cys Glu Ala Met Thr Met Val Cys Ala Gln Val Met Gly Asn Asn
            340                 345                 350

Thr Ala Ile Ser Val Ala Gly Ser Asn Gly Gln Phe Glu Leu Asn Val
        355                 360                 365

Phe Lys Pro Val Met Ile Lys Asn Leu Ile Gln Ser Ile Arg Leu Ile
    370                 375                 380

Ser Asp Ala Ser Ile Ser Phe Thr Lys Asn Cys Val Val Gly Ile Glu
385                 390                 395                 400

Ala Asn Glu Lys Lys Ile Ser Ser Ile Met Asn Glu Ser Leu Met Leu
                405                 410                 415

Val Thr Ala Leu Asn Pro His Ile Gly Tyr Asp Lys Ala Ala Lys Cys
            420                 425                 430

Ala Lys Lys Ala His Lys Glu Gly Thr Thr Leu Lys Glu Ala Ala Leu
        435                 440                 445

Ser Leu Gly Tyr Leu Thr Ser Glu Glu Phe Asp Gln Trp Val Arg Pro
    450                 455                 460

Glu Asp Met Ile Ser Ala Lys Asp
465                 470


<210> SEQ ID NO 9
<211> LENGTH: 365
<212> TYPE: PRT
<213> ORGANISM: Artificial Sequence
<220> FEATURE:
<223> OTHER INFORMATION: Saccharomyces cerevisiae malate dehydrogenase
      lacking first 12 amino acids

<400> SEQUENCE: 9

Met Leu Lys Ile Ala Ile Leu Gly Ala Ala Gly Gly Ile Gly Gln Ser
1               5                   10                  15

Leu Ser Leu Leu Leu Lys Ala Gln Leu Gln Tyr Gln Leu Lys Glu Ser
            20                  25                  30
```

```
Asn Arg Ser Val Thr His Ile His Leu Ala Leu Tyr Asp Val Asn Gln
        35                  40                  45

Glu Ala Ile Asn Gly Val Thr Ala Asp Leu Ser His Ile Asp Thr Pro
    50                  55                  60

Ile Ser Val Ser Ser His Ser Pro Ala Gly Gly Ile Glu Asn Cys Leu
65                  70                  75                  80

His Asn Ala Ser Ile Val Val Ile Pro Ala Gly Val Pro Arg Lys Pro
                85                  90                  95

Gly Met Thr Arg Asp Asp Leu Phe Asn Val Asn Ala Gly Ile Ile Ser
            100                 105                 110

Gln Leu Gly Asp Ser Ile Ala Glu Cys Cys Asp Leu Ser Lys Val Phe
        115                 120                 125

Val Leu Val Ile Ser Asn Pro Val Asn Ser Leu Val Pro Val Met Val
    130                 135                 140

Ser Asn Ile Leu Lys Asn His Pro Gln Ser Arg Asn Ser Gly Ile Glu
145                 150                 155                 160

Arg Arg Ile Met Gly Val Thr Lys Leu Asp Ile Val Arg Ala Ser Thr
                165                 170                 175

Phe Leu Arg Glu Ile Asn Ile Glu Ser Gly Leu Thr Pro Arg Val Asn
            180                 185                 190

Ser Met Pro Asp Val Pro Val Ile Gly Gly His Ser Gly Glu Thr Ile
        195                 200                 205

Ile Pro Leu Phe Ser Gln Ser Asn Phe Leu Ser Arg Leu Asn Glu Asp
    210                 215                 220

Gln Leu Lys Tyr Leu Ile His Arg Val Gln Tyr Gly Gly Asp Glu Val
225                 230                 235                 240

Val Lys Ala Lys Asn Gly Lys Gly Ser Ala Thr Leu Ser Met Ala His
                245                 250                 255

Ala Gly Tyr Lys Cys Val Val Gln Phe Val Ser Leu Leu Leu Gly Asn
            260                 265                 270

Ile Glu Gln Ile His Gly Thr Tyr Tyr Val Pro Leu Lys Asp Ala Asn
        275                 280                 285

Asn Phe Pro Ile Ala Pro Gly Ala Asp Gln Leu Leu Pro Leu Val Asp
    290                 295                 300

Gly Ala Asp Tyr Phe Ala Ile Pro Leu Thr Ile Thr Thr Lys Gly Val
305                 310                 315                 320

Ser Tyr Val Asp Tyr Asp Ile Val Asn Arg Met Asn Asp Met Glu Arg
                325                 330                 335

Asn Gln Met Leu Pro Ile Cys Val Ser Gln Leu Lys Lys Asn Ile Asp
            340                 345                 350

Lys Gly Leu Glu Phe Val Ala Ser Arg Ser Ala Ser Ser
        355                 360                 365


<210> SEQ ID NO 10
<211> LENGTH: 438
<212> TYPE: PRT
<213> ORGANISM: Schizosaccharomyces pombe

<400> SEQUENCE: 10

Met Gly Glu Leu Lys Glu Ile Leu Lys Gln Arg Tyr His Glu Leu Leu
1               5                   10                  15

Asp Trp Asn Val Lys Ala Pro His Val Pro Leu Ser Gln Arg Leu Lys
            20                  25                  30

His Phe Thr Trp Ser Trp Phe Ala Cys Thr Met Ala Thr Gly Gly Val
        35                  40                  45
```

-continued

```
Gly Leu Ile Ile Gly Ser Phe Pro Phe Arg Phe Tyr Gly Leu Asn Thr
    50                  55                  60

Ile Gly Lys Ile Val Tyr Ile Leu Gln Ile Phe Leu Phe Ser Leu Phe
65                  70                  75                  80

Gly Ser Cys Met Leu Phe Arg Phe Ile Lys Tyr Pro Ser Thr Ile Lys
                85                  90                  95

Asp Ser Trp Asn His His Leu Glu Lys Leu Phe Ile Ala Thr Cys Leu
            100                 105                 110

Leu Ser Ile Ser Thr Phe Ile Asp Met Leu Ala Ile Tyr Ala Tyr Pro
        115                 120                 125

Asp Thr Gly Glu Trp Met Val Trp Val Ile Arg Ile Leu Tyr Tyr Ile
    130                 135                 140

Tyr Val Ala Val Ser Phe Ile Tyr Cys Val Met Ala Phe Phe Thr Ile
145                 150                 155                 160

Phe Asn Asn His Val Tyr Thr Ile Glu Thr Ala Ser Pro Ala Trp Ile
                165                 170                 175

Leu Pro Ile Phe Pro Pro Met Ile Cys Gly Val Ile Ala Gly Ala Val
            180                 185                 190

Asn Ser Thr Gln Pro Ala His Gln Leu Lys Asn Met Val Ile Phe Gly
        195                 200                 205

Ile Leu Phe Gln Gly Leu Gly Phe Trp Val Tyr Leu Leu Leu Phe Ala
    210                 215                 220

Val Asn Val Leu Arg Phe Phe Thr Val Gly Leu Ala Lys Pro Gln Asp
225                 230                 235                 240

Arg Pro Gly Met Phe Met Phe Val Gly Pro Pro Ala Phe Ser Gly Leu
                245                 250                 255

Ala Leu Ile Asn Ile Ala Arg Gly Ala Met Gly Ser Arg Pro Tyr Ile
            260                 265                 270

Phe Val Gly Ala Asn Ser Ser Glu Tyr Leu Gly Phe Val Ser Thr Phe
        275                 280                 285

Met Ala Ile Phe Ile Trp Gly Leu Ala Ala Trp Cys Tyr Cys Leu Ala
    290                 295                 300

Met Val Ser Phe Leu Ala Gly Phe Phe Thr Arg Ala Pro Leu Lys Phe
305                 310                 315                 320

Ala Cys Gly Trp Phe Ala Phe Ile Phe Pro Asn Val Gly Phe Val Asn
                325                 330                 335

Cys Thr Ile Glu Ile Gly Lys Met Ile Asp Ser Lys Ala Phe Gln Met
            340                 345                 350

Phe Gly His Ile Ile Gly Val Ile Leu Cys Ile Gln Trp Ile Leu Leu
        355                 360                 365

Met Tyr Leu Met Val Arg Ala Phe Leu Val Asn Asp Leu Cys Tyr Pro
    370                 375                 380

Gly Lys Asp Glu Asp Ala His Pro Pro Pro Lys Pro Asn Thr Gly Val
385                 390                 395                 400

Leu Asn Pro Thr Phe Pro Pro Glu Lys Ala Pro Ala Ser Leu Glu Lys
                405                 410                 415

Val Asp Thr His Val Thr Ser Thr Gly Gly Glu Ser Asp Pro Pro Ser
            420                 425                 430

Ser Glu His Glu Ser Val
        435
```

DICARBOXYLIC ACID PRODUCTION PROCESS

CROSS REFERENCE TO RELATED APPLICATIONS

This application is a §371 National Stage Application of PCT/EP2010/053753, filed Mar. 23, 2010, which claims priority to European Application Nos. 09157694.9, filed Apr. 15, 2009; and Ser. No. 09/169,412.5, filed Sep. 3, 2009, and U.S. Provisional Application No. 61/239,566, filed Sep. 3, 2009.

BACKGROUND OF THE INVENTION

1. Field of the Invention

The present invention relates to a process for the fermentative production of a dicarboxylic acid by yeast and the recovery of the dicarboxylic acid by crystallization.

2. Description of Related Art

Dicarboxylic acids such as malic acid, fumaric acid and succinic acid, are important compounds which are used in the food industry for the preparation and preservation of food, in the medical industry for the formulation of medical products, building blocks in (bio)polymers and other industrial uses. To meet the increasing need for dicarboxylic acids, more efficient and cost effective production methods are being developed.

Bacteria can produce large amounts of dicarboxylic acids. However, one major drawback associated with the use of bacteria for producing dicarboxylic acids is the formation of the acid salt. If bacteria are used, the pH needs to be maintained in the range of pH 6-7. As a consequence, most acids will be produced in their salt form and the salts will have to be converted into the acid. This is not practical or efficient in large-scale production processes and raises production costs. Alternatively, low pH processes are considered to be more attractive, in particular at a large scale.

Yeasts are attractive candidates for low pH dicarboxylic acid production processes. However, at low pH a dicarboxylic acid in the acid form diffuses through the cell membrane inside the cell, whereupon the cell will try to transport the dicarboxylic acid outside the cell. This transport will likely require energy in the form of ATP. Under aerobic conditions, a yeast cell can generate energy in the form of ATP by oxidative respiration. An aerobic process for the production of malic acid and succinic acid by a (genetically modified) yeast is for instance disclosed in WO2007/061590. However, aerobic processes for the production of dicarboxylic acid by yeast fermentation are not desirable since under aerobic conditions the dicarboxylic acid yield on carbon is estimated to be lower than under anaerobic conditions.

Under anaerobic conditions, yeast produces dicarboxylic acid via the reductive tricarboxylic acid cycle, producing 1 mole of ATP, which is considered not to be sufficient for maintenance of the cell and/or transport of the dicarboxylic acid outside the cell. Therefore, the yeast cell will need to use alternative ways to generate energy during anaerobic dicarboxylic acid fermentation, with little to no expense of the dicarboxylic acid yield.

SUMMARY OF THE INVENTION

The aim of the present invention is a process for the production of a dicarboxylic acid by yeast fermentation under anaerobic conditions and at low pH, wherein the dicarboxylic acid is produced at a high amount.

The aim is achieved according to the invention with a process for the production of a dicarboxylic acid and ethanol which comprises fermenting a genetically modified yeast in a suitable fermentation medium under anaerobic conditions at a pH value of between 1 and 5 and producing the dicarboxylic acid and ethanol.

Surprisingly, it was found that ethanol production by the genetically modified yeast in the process according to the present invention produced sufficient ATP for maintenance of the yeast cell and at the same time allowed dicarboxylic acid production at a high amount under anaerobic conditions. The stoichiometric reaction of ethanol from glucose is: 1 glucose→2 ethanol+2$CO_2$+2 ATP.

DETAILED DESCRIPTION OF A PREFERRED EMBODIMENT

WO89/05861 discloses a yeast fermentation process for the production of ethanol and succinic acid. However, the fermentation process disclosed in WO89/05861 resulted in low amounts of succinic acid and high amounts of ethanol.

A high amount of dicarboxylic acid as used herein is defined as an amount of dicarboxylic acid of at least 1 g/l under anaerobic conditions and a pH of between 1 and 5, preferably an amount of at least 2, 5, 10 g/l, preferably at least 12, 15 g/l, more preferably at least 18 g/l, usually below 100 g/l of dicarboxylic acid in the process for the production of dicarboxylic acid and ethanol according to the present invention.

The dicarboxylic acid in the process of the invention preferably is malic acid, fumaric acid or succinic acid, most preferably succinic acid. The term dicarboxylic acid is used to indicate also dicarboxylate, such as malate, fumarate and succinate which are used interchangeably. Dicarboxylate is the ionic form of dicarboxylic acid.

In another embodiment, ethanol in the process according to the present invention is produced in a low amount. A low amount of ethanol as used herein is an amount of below 100 g/l, preferably below 80, 60, 40 g/l, preferably below 35 g/l, preferably below 30 g/l, and usually more than 1 g/l.

It was found advantageous that a lower amount of ethanol was produced by the genetically modified yeast as compared to a wild type yeast since which resulted in the production of a higher amount of dicarboxylic acid.

Another advantage for the production of ethanol in the process for the production of dicarboxylic acid according to the present invention is that simultaneously carbondioxide ($CO_2$) is produced. A higher amount of $CO_2$ leads to a higher production of oxaloacetate from pyruvate, e.g. by phosphoenol pyruvate carboxykinase, which positively influences the production of a dicarboxylic acid in the process according to the present invention.

Another advantage of the process according to the invention was that the process was suitable to be implemented in existing ethanol fermentation facilities.

Surprisingly, it was found that in the process according to the present invention low amounts of by-products such as organic acids were formed. In particular, it was surprisingly found that a low amount of glycerol was formed. A low amount of glycerol is herein defined as a concentration of below 2 g/l, preferably below 1 g/l, preferably below 0.5 g/l, usually above 0.01 g/l.

The process for the production of dicarboxylic acid and ethanol according to the present invention may be carried out in any suitable mode, such as a batch, fed-batch, continuous mode or a combination of these fermentation modes. Preferably, the process for the production of dicarboxylic acid and ethanol according to the present invention is carried out in a fed-batch mode or continuous mode.

In one embodiment fermenting the yeast in the process of the invention is carried out under carbohydrate limiting conditions. As used herein, carbohydrate limiting conditions are defined as maintaining the carbohydrate concentration below 10 g/l, preferably below 5 g/l preferably below 2 g/l, usually above 0.5 g/l.

The process for the production of dicarboxylic acid and ethanol according to the present invention may be carried out in any suitable volume and scale, preferably on an industrial scale. Industrial scale is defined herein as a volume of at least 10, or 100 liters, preferably at least 1 cubic meter, preferably at least 10, or 100 cubic meters, preferably at least 1000 cubic meters, usually below 10,000 cubic meters.

Fermenting the genetically modified yeast in the process of the invention may be carried out in any suitable fermentation medium comprising a suitable nitrogen source, carbohydrate and other nutrients required for growth and production of a dicarboxylic acid and ethanol in the process of the invention. A suitable carbohydrate in the fermentation process according to the invention may be glucose, galactose, xylose, arabinose, sucrose, or maltose.

An anaerobic fermentation process is herein defined as a fermentation process run in the absence of oxygen, and wherein organic molecules serve as both electron donor and electron acceptor.

In one embodiment, the fermentation process is carried out under a partial $CO_2$ pressure of between 5% and 50%, preferably between 10% and 40%.

The pH during the process for the production of dicarboxylic acid and ethanol usually lowers during the production of the dicarboxylic acid. Preferably, the pH in the process for the production of dicarboxylic acid and ethanol ranges between 1 and 5, preferably between 1.5 and 4.5, more preferably between 2 and 4.

In another preferred embodiment the process according to the present invention comprises a step of preculturing the genetically modified yeast under aerobic conditions in the presence of a carbohydrate. Preferably, the fermenting of the yeast is carried out at a pH of between 4 and 6. Preferably, the carbohydrate during preculturing is a non-repressing carbohydrate, preferably galactose. It was found advantageous to preculture yeast on a non-repressing carbohydrate, since this prevented glucose repression to occur in yeast, which negatively influences the amount of dicarboxylic acid produced. In addition, it was found that a step of preculturing the yeast under aerobic conditions resulted in a higher biomass yield and a faster growth. Preferably, the preculturing is carried out in batch mode.

A genetically modified yeast in the process of the invention, may comprise any suitable genetic modifications, such as deletions or disruptions, and insertions of homologous or heterologous nucleotides sequences. A yeast in the process of the invention may be genetically modified or transformed with nucleotide sequences that encode homologous and/or heterologous enzymes that catalyse reactions in the cell resulting in an increased flux towards a dicarboxylic acid such malic acid, fumaric acid and/or succinic acid. It may for example be favourable to introduce and/or overexpress nucleotide sequences encoding i) a malate dehydrogenase which catalyses the conversion from OAA to malic acid; ii) a fumarase, which catalyses the conversion of malic acid to fumaric acid; or iii) a fumarate reductase that catalyses the conversion of fumaric acid to succinic acid, depending on the dicarboxylic acid to be produced.

It was found that a genetically modification of a yeast cell in a process according to the present invention was essential to obtain a high amount of dicarboxylic acid and a low amount of ethanol. Preferably, a yeast cell in the process according to the present invention comprises genetic modifications according to the preferred embodiments as described herein below.

Preferably the genetically modified yeast expresses a nucleotide sequence encoding a phosphoenolpyruvate (PEP) carboxykinase in the cytosol. Preferably a nucleotide sequence encoding a phosphoenolpyruvate (PEP) carboxykinase is overexpressed. The PEP carboxykinase (EC 4.1.1.49) preferably is a heterologous enzyme, preferably derived from bacteria, more preferably the enzyme having PEP carboxykinase activity is derived from *Escherichia coil, Mannheimia* sp., *Actinobacillus* sp., or *Anaerobiospirillum* sp., more preferably *Mannheimia succiniciproducens*. Preferably, a yeast cell according to the present invention is genetically modified with a PEP carboxykinase which has at least 80, 85, 90, 95, 99 or 100% sequence identity with amino acid sequence of SEQ ID NO: 6.

In another preferred embodiment a genetically modified yeast in the process according to the present invention further expresses a nucleotide sequence encoding a malate dehydrogenase (MDH; E.C. 1.1.1.37) which is active in the cytosol upon expression of the nucleotide sequence. Preferably the malate dehydrogenase is overexpressed. A cytosolic MDH may be any suitable homologous or heterologous malate dehydrogenase. Preferably, the MDH is *S. cerevisiae* MDH2 which has been modified such that it is not inactivated in the presence of glucose and is active in the cytosol. It is known that the transcription of MDH2 is repressed and Mdh2p is degraded upon addition of glucose to glucose-starved cells. Mdh2p deleted for the first 12 amino-terminal amino acids is less-susceptible for glucose-induced degradation (Minard and McAlister-Henn, J. Biol Chem. 1992 Aug. 25; 267(24): 17458-64). Preferably, a yeast cell according to the present invention comprises a nucleotide sequence encoding a malate dehydrogenase that has at least 70%, preferably at least 75, 80, 85, 90, 92, 94, 95, 96, 97, 98, 99% or 100% sequence identity with the amino acid sequence of SEQ ID NO: 9.

In another preferred embodiment a genetically modified yeast in the process according to the present invention expresses a nucleotide sequence encoding a fumarase (E.C. 4.2.1.2.) in the cytosol, which may be a heterologous or homologous enzyme. Preferably a nucleotide sequence encoding a fumarase is overexpressed. A nucleotide sequence encoding an heterologous fumarase may be derived from any suitable origin, preferably from microbial origin, preferably from a yeast, for instance *Saccharomyces cerevisiae* or a filamentous fungus, for instance *Rhizopus oryzae*. Preferably, a yeast in the process according to the present invention overexpresses a nucleotide sequence encoding a fumarase that has at least 70%, preferably at least 75, 80, 85, 90, 92, 94, 95, 96, 97, 98, or 99% or 100% sequence identity with the amino acid sequence of SEQ ID NO: 8.

In another preferred embodiment a genetically modified yeast in the process according to the present invention expresses a nucleotide sequence encoding a fumarate reductase (E.C. 1.3.1.6) in the cytosol. Preferably, the fumarate reductase is a heterologous enzyme, preferably a NAD(H)-dependent fumarate reductase, which may be derived from any suitable origin, for instance bacteria, fungi, protozoa or plants. Preferably, the (NAD(H)-dependent) fumarate reductase is overexpressed. Preferably, a yeast in the process according to the invention comprises a heterologous NAD (H)-dependent fumarate reductase, preferably derived from a

*Trypanosoma* sp, for instance a *Trypanosoma brucei*. Preferably, a yeast cell according to the present invention is genetically modified with a NAD(H)-dependent fumarate reductase, which has at least 80, 85, 90, 95, 99 or 100% sequence identity with SEQ ID NO: 7.

In another embodiment, a genetically modified yeast in the process according to the invention expresses a nucleotide sequence encoding a dicarboxylic acid transporter protein, preferably a malic acid transporter protein (MAE) in the cytosol. Preferably the dicarboxylic acid transporter protein is overexpressed. A dicarboxylic acid transporter protein may be any suitable homologous or heterologous protein. Preferably the dicarboxylic acid transporter protein is a heterologous protein. A dicarboxylic acid transporter protein may be derived from any suitable organism, preferably from yeast or fungi such as *Schizosaccharomyces pombe*. Preferably, a dicarboxylic acid transporter protein is a malic acid transporter protein (MAE) which has at least 80, 85, 90, 95 or 99% or 100% sequence identity with SEQ ID NO: 10.

Preferably, the yeast in the process of the invention comprises at least one gene encoding glycerol-3-phosphate dehydrogenase which is not functional. A glycerol-3-phosphate dehydrogenase gene that is not functional is used herein to describe a eukaryotic cell, which comprises a reduced glycerol-3-phosphate dehydrogenase activity, for instance by mutation, disruption, or deletion of the gene encoding glycerol-3-phosphate dehydrogenase, resulting in a decreased formation of glycerol as compared to a wild-type cell.

Preferably, a genetically modified yeast in the process according to the present invention overexpresses a nucleotide sequence encoding a PEP carboxykinase, a nucleotide sequence encoding a malate dehydrogenase, a nucleotide sequence encoding a fumarase, a nucleotide sequence encoding a NAD(H) dependent fumarate reductase, and/or a nucleotide sequence encoding a malic acid transporter protein, preferably wherein the enzymes are active in the cytosol. Preferred embodiments of the enzymes are as described herein above.

As used herein, a genetically modified yeast according to the present invention is defined as a cell which contains, or is transformed or genetically modified with or a nucleotide sequence or polypeptide that does not naturally occur in the yeast cell, or it contains additional copy or copies of an endogenous nucleic acid sequence, or it contains a deletion or disruption of an endogenous or homlogous nucleotide sequence. A wild-type eukaryotic cell is herein defined as the parental cell of the recombinant cell.

The term "homologous" when used to indicate the relation between a given (recombinant) nucleic acid or polypeptide molecule and a given host organism or host cell, is understood to mean that in nature the nucleic acid or polypeptide molecule is produced by a host cell or organism of the same species, preferably of the same variety or strain.

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but have been obtained from another cell or synthetically or recombinantly produced.

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Preferred methods to determine identity are designed to give the largest match between the sequences tested. Methods to determine identity and similarity are codified in publicly available computer programs. Preferred computer program methods to determine identify and similarity between two sequences include BLASTP and BLASTN, publicly available from NCBI and other sources (BLAST Manual, Altschul, S., et al., NCBI NLM NIH Bethesda, Md. 20894). Preferred parameters for amino acid sequences comparison using BLASTP are gap open 11.0, gap extend 1, Blosum 62 matrix.

The term "nucleic acid" as used herein, includes reference to a deoxyribonucleotide or ribonucleotide polymer, i.e. a polynucleotide, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof.

There are various means available in the art for overexpression of nucleotide sequences encoding enzymes in a yeast in the process of the invention. In particular, a nucleotide sequence encoding an enzyme may be overexpressed by increasing the copy number of the gene coding for the enzyme in the cell, e.g. by integrating additional copies of the gene in the cell's genome, by expressing the gene from a centromeric vector, from an episomal multicopy expression vector or by introducing an (episomal) expression vector that comprises multiple copies of the gene. Preferably, overexpression of the enzyme according to the invention is achieved with a (strong) constitutive promoter.

The yeast in the process for the production of a dicarboxylic acid and ethanol according to the present invention preferably belongs to one of the genera *Schizosaccharomyces, Saccharomyces, Yarrowia, Candida, Pichia, Kluyveromyces, Issatchenko* or *Zygosaccharomyces*. More preferably, the yeast is a *Saccharomyces cerevisiae, Saccharomyces uvarum, Saccharomyces bayanus, Yarrowia lipolytica, Candida sonorensis, Schizosaccharomyces pombe, Pichia stipidis, Kluyveromyces marxianus, K. lactis, K. thermotolerans, Issatchenko orientalis* or *Zygosaccharomyces bailii.*

In another aspect the present invention relates to a process for producing a fermentation product by a genetically modified yeast, wherein ethanol production in the yeast is used to generate energy in the form of ATP under anaerobic conditions and a pH of between 1 and 5 in a suitable fermentation medium, and wherein the yeast comprises a genetic modification that increases the production of the fermentation product as compared to a yeast not comprising said genetic modification. Surprisingly it was found that under low pH and anaerobic conditions production of ethanol, preferably a low amount of ethanol resulted in a high amount of fermentation product.

Preferably, the fermentation product is a dicarboxylic acid, preferably malic acid, fumaric acid or succinic acid. Preferred embodiments of the process for producing a fermentation product are further as defined herein for the process for the production of dicarboxylic acid and ethanol.

In a preferred embodiment the process for the production of a dicarboxylic acid and ethanol further comprises recovering the dicarboxylic acid and/or ethanol. Recovery of the dicarboxylic acid and ethanol may be carried out by any suitable method. Preferably, ethanol is recovered by distillation from the fermentation medium.

In a preferred embodiment the recovering of dicarboxylic acid comprises crystallizing the dicarboxylic acid and forming dicarboxylic acid crystals. Preferably, the crystallizing of dicarboxylic acid comprises removing part of the fermentation medium, preferably by evaporation, to obtain a concentrated medium.

In a preferred embodiment the process according to the present invention comprises recovering a dicarboxylic acid which is a succinic acid and wherein the recovering comprises crystallizing succinic acid from an aqueous solution having a pH of between 1 and 5 and comprising succinic acid, comprising evaporating part of the aqueous solution to obtain a concentrated solution, lowering the temperature of the concentrated solution to a value of between 5 and 35 degrees Celsius, wherein succinic acid crystals are formed. Preferably, the crystallizing comprises bringing the temperature of the concentrated medium to a temperature of between 10 and 30 degrees Celsius, preferably between 15 and 25 degrees Celsius. Preferably, the fermentation medium has a pH of between 1.5 and 4.5, preferably between 2 and 4.

It was found that crystallizing succinic acid at higher temperatures such as between 10 and 30 degrees Celsius resulted in succinic acid crystals with a lower amount of impurities such as organic acid, protein, color and/or odor, than succinic acid crystals that were crystallized at a low temperature of below 10 degrees.

Another advantage of crystallizing succinic acid at a higher temperature was that it requires a lower amount of energy for cooling the aqueous solution as compared to a process wherein crystallizing succinic acid is carried out below 10 or 5 degrees Celsius, resulting in a more economical and sustainable process.

Preferably, the crystallizing of succinic acid comprises a step of washing the succinic acid crystals.

Surprisingly it was found that it was possible to crystallize succinic acid directly from the fermentation medium having a pH of between 1 and 5 to a purity of at least 90% w/w, preferably at least 95, 96, 97, or at least 98%, or 99 to 100% w/w.

Preferably, the recovering of the dicarboxylic acid and ethanol, preferably succinic acid and ethanol, comprises removing the biomass from the fermentation medium, distilling ethanol from the fermentation medium and crystallizing the dicarboxylic acid, preferably crystallizing as described herein above. Preferably, the removing of biomass is carried out by filtration.

In a preferred embodiment the process for the production of a dicarboxylic acid and ethanol further comprises using the dicarboxylic acid and ethanol in an industrial process. An industrial process for a dicarboxylic acid may be the application as a cosmetic additive, deicing agent, food additive or as a building block for (bio)polymers. Industrial processes for ethanol may be the application as a solvent or as a biofuel.

In a preferred embodiment the fermentation medium comprises an amount of succinic acid of between 1 and 150 g/l, preferably between 5 and 100 g/l, more preferably between 10 and 80 g/l or between 15 and 60 g/l of succinic acid.

In another aspect the present invention relates to a process for crystallizing succinic acid from an aqueous solution having a pH of between 1 and 5 and comprising succinic acid, comprising removing part of the aqueous solution by evaporation to obtain a concentrated solution, and bringing the temperature of the concentrated solution to a value of between 10 and 30 degrees Celsius, wherein succinic acid crystals are formed. Preferably, the crystallizing comprises bringing the temperature of the concentrated solution between 15 and 25 degrees Celsius, preferably between 18 and 22 degrees Celsius. Preferably, the aqueous solution has a pH of between 1.5 and 4.5, preferably between 2 and 4. The aqueous solution may be any suitable solution comprising succinic acid. The aqueous solution may comprise soluble constituents and insoluble constituents and, such as (fragments of) microbial cells, protein, plant biomass lignocellulose, cellulose and the like. Preferably the aqueous solution is a fermentation medium, preferably a fermentation medium obtainable by a process for the production of a dicarboxylic acid as described herein.

Genetic Modifications

Standard genetic techniques, such as overexpression of enzymes in the host cells, genetic modification of host cells, or hybridisation techniques, are known methods in the art, such as described in Sambrook and Russel (2001) "Molecular Cloning: A Laboratory Manual (3rd edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation, genetic modification etc of fungal host cells are known from e.g. EP-A-0 635 574, WO 98/46772, WO 99/60102 and WO 00/37671, WO90/14423, EP-A-0481008, EP-A-0635 574 and U.S. Pat. No. 6,265,186.

The following examples are for illustrative purposes only and are not to be construed as limiting the invention.

EXAMPLES

Example 1

Construction Yeast Strain 1.1. Construction of Expression Constructs

The expression construct pGBS414PEK-2 was created after a BamHI/NotI restriction of the *S. cerevisiae* expression vector pRS414 (Sirkoski R. S. and Hieter P. Genetics, 1989, 122(1):19-27) and subsequently ligating in this vector a BamHI/NotI restriction fragment consisting of the phosphoenolpyruvate carboxykinase (origin *Mannheirnia succiniciproducens*) synthetic gene construct (SEQ ID NO: 1). The ligation mix was used for transformation of *E. coli* TOP10 (Invitrogen) resulting in the yeast expression construct pGBS414PEK-1 Subsequently, pGBK414PEK-1 was restricted with AscI and NotI. To create pGBS414PEK-2, an AscI/NotI restriction fragment consisting of mitochondrial fumarate reductase from *T. brucei* (FRDm1) synthetic gene construct (SEQ ID NO: 2) was ligated into the restricted pGBS414PEK-1 vector. The ligation mix was used for transformation of *E. coli* TOP10 (Invitrogen) resulting in the yeast expression construct pGBS414PEK-2.

The expression construct pGBS415FUM-2 was created after a BamHI/NotI restriction of the *S. cerevisiae* expression vector pRS415 (Sirkoski R. S. and Hieter P. Genetics, 1989, 122(11:19-27) and subsequently ligating in this vector a BamHI/NotI restriction fragment consisting of the fumarase (origin *Rhizopus oryzae*) synthetic gene construct (SEQ ID NO: 3). The ligation mix was used for transformation of *E. coli* TOP10 (Invitrogen) resulting in the yeast expression construct pGBS415FUM-1. Subsequently, pGBK415FUM-1 was restricted with AscI and NotI. To create pGBS415FUM-2, an AscI/NotI restriction fragment consisting of modified cytoplasmic malate dehydrogenase from *S. cerevisiae* (delta12N MDH2) synthetic gene construct (SEQ ID NO: 4) was ligated into the restricted pGBS415FUM-1 vector. The ligation mix was used for transformation of *E. coli* TOP10 (Invitrogen) resulting in the yeast expression construct pGBS415FUM-2.

The expression construct pGBS416MAE-1 was created after a BamHI/NotI restriction of the *S. cerevisiae* expression vector pRS416 (Sirkoski R. S. and Hieter P. Genetics, 1939, 122(1)19-27) and subsequently ligating in this vector a BamHI/NotI restriction fragment consisting of the *Schizosaccharomyces pombe* malate transporter synthetic gene construct (SEQ ID NO: 5). The ligation mix was used for transformation of *E. coli* TOP10 (Invitrogen) resulting in the yeast expression construct pGBS416MAE-1.

1.2. Construction *S. cerevisiae* Strain

Plasmids pGBS414PEK-2, pGBS415FUM-2 and pGBS416MAE-1 (described under 1.1.) were transformed into *S. cerevisiae* strain CEN.PK113-6B (MATA ura3-52 leu2-112 trp1-289) to create strain SUC-194, overexpressing PCKm, delta12NMDH2, FUMR, FRDm1 and SpMAE1. All genes were codon pair optimized for expression in *S. cerevisiae* according to WO2008/000632.

The expression vectors were transformed into yeast by electroporation. The transformation mixtures were plated on Yeast Nitrogen Base (YNB) w/o AA (Difco)+2% glucose.

Example 2

Anaerobic Succinic Acid and Ethanol Production at Low pH

The *S. cerevisiae* yeast strain SUC-194 (MATA ura3-52 leu2-112 trp1-289, overexpressing SpMAE1, PCKm, delta12NMDH2, FUMR and FRDm1) was cultivated in shake-flask (2×300 ml) for 3 days at 30° C. and 220 rpm. The medium was based on Verduyn, but modifications in carbon and nitrogen source were made as shown in Table 1-3.

TABLE 1

Preculture shake flask medium composition

| Raw material | Concentration (g/l) |
|---|---|
| Galactose ($C_6H_{12}O_6 \cdot H_2O$) | 20.0 |
| Urea $(NH_2)_2CO$ | 2.3 |
| $KH_2PO_4$ | 3.0 |
| $MgSO_4 \cdot 7H_2O$ | 0.5 |
| Trace element solution[a] | 1 |
| Vitamin solution[b] | 1 |

TABLE 2

[a]Vitamin solution

| Component | Formula | Concentration (g/kg) |
|---|---|---|
| Biotin (D−) | $C_{10}H_{16}N_2O_3S$ | 0.05 |
| Ca D(+) panthothenate | $C_{18}H_{32}CaN_2O_{10}$ | 1.00 |
| Nicotinic acid | $C_6H_5NO_2$ | 1.00 |
| Myo-inositol | $C_6H_{12}O_6$ | 25.00 |
| Thiamine chloride hydrochloride | $C_{12}H_{18}Cl_2N_4OS \cdot xH_2O$ | 1.00 |
| Pyridoxol hydrochloride | $C_8H_{12}ClNO_3$ | 1.00 |
| p-aminobenzoic acid | $C_7H_7NO_2$ | 0.20 |

TABLE 3

[b]Trace elements solution

| Component | Concentration (g/kg) |
|---|---|
| EDTA ($C_{10}H_{14}N_2Na_2O_8 \cdot 2H_2O$) | 15.00 |
| $ZnSO_4 \cdot 7H_2O$ | 4.50 |
| $MnCl_2 \cdot 2H_2O$ | 0.84 |
| $CoCl_2 \cdot 6H_2O$ | 0.30 |
| $CuSO_4 \cdot 2H_2O$ | 0.30 |
| $Na_2MoO_4 \cdot 2H_2O$ | 0.40 |
| $CaCl_2 \cdot 2H_2O$ | 4.50 |
| $FeSO_4 \cdot 7H_2O$ | 3.00 |
| $H_3BO_3$ | 1.00 |
| KI | 0.10 |

Subsequently, the content of the shake-flasks was transferred to 10 L fermenter (Startweight 6 kg), which contained the medium with the composition shown in Table 4:

TABLE 4

Composition medium in fermenter

| Raw material | Concentration (g/l) |
|---|---|
| $(NH_4)_2SO_4$ | 2.5 |
| $KH_2PO_4$ | 3.0 |
| $MgSO_4 \cdot 7H_2O$ | 0.5 |
| Trace element solution[b] | 1 |
| Vitamin solution[a] | 1 |

During the first 24 hours of the fermentation aerobic conditions (0.33 vvm gasflow, controlled OUR of 30 mmol/h and 10% $CO_2$) were applied to generate sufficient biomass. The pH was controlled at 5.0 by addition of 6 N KOH. The temperature was controlled at 30° C. Glucose concentration was kept limited by controlled feed to the fermenter.

After 24 hours the conditions were switched b anaerobic conditions (0.33 vvm, 10% $CO_2$ and 90% $N_2$) and pH control was released.

2.1. NMR Analyses

Dicarboxylic acid concentrations in the fermentation supernatant were determined by means of NMR spectroscopy.

3 ml broth was centrifuged for 10 min at 4500×g. Approximately 500 microliters of supernatant were accurately weighed to a headspace vial. To each sample 0.5 ml of pen buffer C-2696 (containing 5.62 mg/ml maleic acid) was added. The samples were capped and cooked for about 10 minutes in a water bath (and in oil bath in the control sample CF292706-11 and CF292706-12) at 100° C. The samples were lyophilized, the residue was dissolved in 1 ml $D_2O$.

The spectra were recorded at a proton frequency of Bruker DRX 360 MHz at a probe temperature of 300 K. The quantitative measurements were performed with pulse program zg, excitation pulse from 30-90 degrees and a relaxation delay of 40 s. Ethanol and glycerol concentrations were measured using flow-NMR. To 900 microliters supernatant 100 microliters of 20 g/l maleic acid in $D_2O$ containing 40 g/l EDTA were added. The samples were homogenized and measured with an Avance II 500 MHz BEST NMR, equipped with a cryprobe, operating at 500 MHz and temperature of 27° C. The pulse program noesygppr1d.comp was used with relaxation delay of 30 s, ns=4, ds=0, and water suppression power level pl9=65 dB.

During the anaerobic cultivation the pH decreased to 3.25 after 90 hours of cultivation. After this period 19.5 g/l, succinic acid, 25.1 g/l ethanol and minimal levels of glycerol and malic acid were produced (both 0.5 g/L).

Example 3

Recovery of Succinic Acid Crystals from Fermentation Broth 3.1.

The broth obtained from the anaerobic fermentation process as described in example 2 was filtered on a pressure filter (Pall Z200 filter and subsequent Pall Z2000 filter). The obtained clear filtrate was concentrated by water evaporation at 80° C. under mild vacuum until crystallization on-set was observed (visually). The concentrate was cooled to 20° C., yielding succinic acid crystals. The slurry was filtered on a glass filter (Nr 2 standard glass filter) and the obtained succinic acid wet cake was washed with 1 bed volume of cold (5° C.) demineralized water. The washed cake was dried in a vacuum stove for 24 hours.

NMR analysis indicated a purity in excess of 98% w/w in succinic acid on dry weight basis. The recovery yield of succinic acid was in excess of 80%.

3.2.

A second fermentation broth from anaerobic yeast fermentation as described in Example 2 was collected. The broth pH was 3.1. The broth was centrifuged at 4000 G for 10 minutes to remove suspended biomass. The supernatant was collected and filtered on a polish filter (Pall 77000 and Pall Z200) to remove residual suspended solids. A total of 5.5 kg of filtrate was collected, containing 15.7 gram succinic acid per liter. The filtrate was concentrated by a factor 16 by evaporation under mild vacuum (80° C.). During concentration residual traces of precipitate which were removed by filtration on filter cloth. Analysis indicated that the composition of the precipitate was >95% calcium sulphate.

The filtered concentrate was subsequently cooled to 20° C., allowing the succinic acid to crystallize. The crystals in the slurry were recovered by filtration on filter cloth. The recovered crystals were washed with 1 bed volume of demineralized water and dried. A total of 53 gram of crystals was recovered, corresponding to a recovery yield of 61% w/w. Proton NMR analysis as described in Example 2.1. indicated that the crystals contained >99.3% w/w of succinic acid on dry weight basis.

The combined mother liquor (215 gram, pH 3.5), spent wash water (86 gram. pH 3.1) and equipment rinse water were collected and subsequently concentrated by evaporation and subsequently cooled to 20° C. as described above. A second crop of crystals was recovered and washed with 1 bed volume of demineralised water. The second crop of crystals (11.6 gram on dry weight) contained over 96% w/w succinic acid on dry weight basis.

The total recovery yield of both crops was calculated at 74% with an average purity of 99%.

The results in Example 3 show that it was possible to obtain high purity succinic acid crystals in a high amount in a simple and economical one-step crystallization process which did not require the addition of salts.

Example 4

Recovery of Succinic Acid from Complex Medium 500 ml of a model solution of a dry-grind bioethanol refinery of thin stillage as described by Kim et al. (Bioresource Technology 99 (2008), pages 5165-5176) was spiked with succinic acid. The pH of the stillage was between 3 and 4. The solids in the thin stillage were filtered off by pressure filtration (Pall Z200 and Z2000 pressure filtration), yielding a clear filtrate. The filtrate was concentrated by evaporation of water at 80° C. under mild vacuum, until the liquid became turbid (determined visually). The hot liquid was filtered (Pall Z200 filter) at 80° C. to remove precipitated substances and subsequently cooled. The slurry was filtered over a glass filter (nr 2 standard glass filter). The obtained filter cake was washed with 1 bed volume of cold (5° C.) demineralized water. The obtained crystals were dried for 24 h in a vacuum stove. NMR analysis of the dried crystals indicated a purity in excess of 98% w/w in succinic acid. The yield in was ~50% in succinic acid.

The invention claimed is:

1. A process for the production of a dicarboxylic acid and ethanol which comprises fermenting a genetically modified yeast in a fermentation medium under anaerobic conditions at a pH value of between 1 and 5 and producing the dicarboxylic acid and ethanol, wherein the dicarboxylic acid is selected from the group consisting of: malic acid, fumaric acid, and succinic acid, and wherein the genetically modified yeast is transformed with at least one nucleotide encoding an enzyme expressed in the cytosol selected from the group consisting of: phosphoenol pyruvate carboxykinase, malate dehydrogenase, fumarase, and fumarate reductase.

2. The process according to claim 1 wherein the amount of dicarboxylic acid produced is at least 1 g/l.

3. The process according to claim 1, wherein the amount of ethanol produced is below 100 g/l.

4. The process according to claim 1, wherein the process further comprises preculturing the genetically modified yeast under aerobic conditions in the presence of a carbohydrate.

5. The process according to claim 1, wherein the yeast expresses a nucleotide sequence encoding a phosphoenol pyruvate carboxykinase in cytosol.

6. The process according to claim 1, wherein the yeast expresses a nucleotide sequence encoding a malate dehydrogenase in cytosol.

7. The process according to claim 1, wherein the yeast expresses a nucleotide sequence encoding a fumarase in cytosol.

8. The process according to claim 1, wherein the yeast expresses a nucleotide sequence encoding a fumarate reductase in cytosol.

9. The process according to claim 1, further comprising recovering the dicarboxylic acid and/or ethanol.

10. The process according to claim 9, wherein the dicarboxylic acid is succinic acid and further wherein the recovering comprises crystallizing succinic acid from a fermentation medium having a pH of between 1 and 5 and comprising succinic acid, and further comprising removing at least a part of the fermentation medium by evaporation to obtain a concentrated solution, and bringing a temperature of the concentrated solution to a value of between 5 and 35 degrees Celsius, wherein succinic acid crystals are formed.

11. The process according to claim 9, further comprising using the dicarboxylic acid and/or ethanol in an industrial process.

12. The process according to claim 1, wherein the process is carried out on an industrial scale.

* * * * *